US00PP14266P39

(12) United States Plant Patent
van Rijsselberghe

(10) Patent No.: US PP14,266 P3
(45) Date of Patent: Nov. 4, 2003

(54) PHALAENOPSIS PLANT NAMED 'OSIRIS'

(50) Latin Name: *Phalaenopsis sp.*
Varietal Denomination: Osiris

(75) Inventor: Ronie van Rijsselberghe, Lochristi (BE)

(73) Assignee: Microflor NV, Lochristi (BE)

( * ) Notice: Subject to any disclaimer, the term of this patent is extended or adjusted under 35 U.S.C. 154(b) by 0 days.

(21) Appl. No.: 10/090,770

(22) Filed: Mar. 6, 2002

(65) Prior Publication Data

US 2003/0172425 P1 Sep. 11, 2003

(51) Int. Cl.[7] ..... A01H 5/00
(52) U.S. Cl. ..... Plt./311

(58) Field of Search ..... Plt./311

(56) References Cited

U.S. PATENT DOCUMENTS

PP13,048 P2 * 10/2002 van Rijsselberghe ..... Plt./311

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct cultivar of Phalaenopsis orchid named 'Osiris' characterized by broad elliptic leaves; brown stem; showy light purple flowers with dark purple stripes and white margins; dull, green leaves with silvery glance and purple spots; and freely flowering with 10–15 flowers and buds per raceme.

2 Drawing Sheets

Latin name of the genus and species of the plant claimed: Phalaenopsis sp.
Variety denomination: 'Osiris'.

BACKGROUND OF THE INVENTION

The present invention comprises a new and distinct cultivar of Phalaenopsis orchid, hereinafter referred to by the cultivar name 'Osiris'. The genus Phalaenopsis is a member of the family Orchidaceae.

Phalaenopsis comprises a genus of about 55 species of herbaceous perennials many of which, or the hybrids thereof, are suitable for cultivation in the home or greenhouse. Phalaenopsis is predominantly epiphytic or rock-dwelling, and is native to tropical Asia, Malay Archipelago and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

Phalaenopsis orchids, often referred to as 'Moth Orchids' in the horticultural trade, are frequently used to furnish cut flowers for the florist trade or sold as flowering potted-plants for home or interior scape.

Phalaenopsis produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate.

The new cultivar is a product of a breeding program carried out by the inventor, Ronie van Rijsselberghe. The new cultivar is a result of a cross of two unnamed non-commercial varieties owned by the applicant made in September 1993. The new cultivar 'Osiris' was selected from the progeny of the stated cross in Lochristi by the inventor in March 1996.

Asexual propagation by tissue culture, performed by the inventor in Lochristi, Belgium in March 1996, was used to increase the number of plants for evaluation and has demonstrated that the combination of characteristics as here in disclosed for 'Osiris' are firmly fixed and are retained through successive generations of asexual reproduction.

BRIEF DESCRIPTION OF THE INVENTION

The following traits have been repeatedly observed to be characteristics which in combination distinguish 'Osiris' from generally available seedling-derived Phalaenopsis common in commercial cultivation:

1. broad elliptic leaves;
2. brown stem;
3. showy light purple flowers with dark purple stripes and white margins;
4. dull, green leaves with silvery glance and purple spots; and
5. freely flowering with 10–15 flowers and buds per raceme.

'Osiris' has not been observed under all possible environmental conditions. The phenotype may vary significantly with variations in environment such as temperature, light intensity, fertilization and day length without any change in the genotype. The following observations, measurements and values describe plants grown in Lochristi, Belgium under a glass covered greenhouse in a 12 cm container under conditions which approximate commercial Phalaenopsis production conditions. Plants were grown for about 45 weeks after planting. During the first 25 weeks of production, day and night temperatures averaged 25 degrees Celsius; during the next four weeks of production, day and night temperatures averaged 18 degrees Celsius; and for the last weeks of production, day and night temperatures averaged 20 degrees Celsius. Lowest temperature tolerance is 15 degrees Celsius, highest is 38 degrees Celsius.

Perhaps the closest commercial comparison to 'Osiris' can be made to 'Artemisa' (U.S. Plant Pat. No. 13,048). In side-by-side comparisons conducted in Rijswijk, The Netherlands, plants of the new Phalaenopsis differ from 'Artemisa' in the following ways. The leaves have a midrib which has the same color as the rest of the leaf whereas the midrib of 'Artemisa' is dark purple. The leaves of 'Artemisa' are glossy green whereas the leaves of 'Osiris' are green, dull with a silvery glance. The underside of the leaf of 'Artemisa' is green with purple spots and a purple margin and midrib whereas the leaf of 'Osiris' is green with a smaller purple margin. The inflorescence stem of 'Artemisa' is darker than the inflorescence stem of 'Osiris'. The flowers of 'Artemisa' are much darker purple than the flowers of 'Osiris' which also have white margins. The petals of 'Artemisa' are a darker purple than the petals of 'Osiris'. 'Artemisa' has a much shorter stem and starts producing flowers much lower on the stem (approximately 10 cm) than 'Osiris'.

BRIEF DESCRIPTION OF THE DRAWING

The accompany photographic illustrations show typical plant and flower characteristics of 'Osiris' with colors being as true as possible with illustrations of this type. The photographs were taken approximately noon on Dec. 28, 2001 in Rijswijk, The Netherlands grown under appropriate growing conditions.

The first drawing shows a 50-week old plant on the left and a close up of the inflorescence to the right.

The second drawing (left side) shows a comparison photo of a 50-month old plant of 'Osiris' to the right and the cultivar 'Artemisa' to the left.

The photo in the right upper corner shows a close-up comparison of 'Artemisa' (right) and 'Osiris' (left).

The photo in the right lower corner shows a close-up of the leaves ('Osiris' upper and 'Artemisa' lower).

DETAILED BOTANICAL DESCRIPTION

All color references are measured against The Royal Horticultural Society (R.H.S.) Colour Chart. Colors are approximate as color depends on horticultural practices such as light level and fertilization rate, among others, without, however any change in genotype.

Propagation: Asexual propagation by tissue culture.

Plant: Under appropriate growing conditions, plants attain a mature size of 60 cm in height and 40 cm in width.

*Vigor.*—Moderate.

Leaves:

*Form.*—The leaf blade is shaped obovate with an obtuse to abruptly acute apex and a cuneate base. The margins are entire. The midrib is furrowed. The leaf blade is smooth and leathery on both sides. The upper leaf surface is smooth, slightly furrowed and leathery. The leaves are smooth and very leathery.

*Size.*—Leaf blades of a mature-sized plant are 19 cm (average) in length and 6.8 cm (average) in width.

*Veins.*—Venation parallel, midrib furrowed, veins upper side green; in between R.H.S. 139A and R.H.S. 147A (Yellow-green Group), but darker; under side yellow-green; R.H.S. 146A.

*Color.*—Mature Leaf Upper surface: Green to yellow-green; from R.H.S. 139A to R.H.S. 146A, irregularly dotted and splashed greyed-green; R.H.S. 191A. Mature Leaf Lower surface: Yellow-green; varying between R.H.S. 146A and R.H.S. 146B. Immature Leaf Upper surface: Green to yellow-green; from R.H.S. 139A to R.H.S. 146A, irregularly dotted and splashed greyed-green; R.H.S. 191A. The greyed-green parts are covering a smaller percentage of the leaf blade as in mature leaves. Immature Leaf Lower surface: Yellow-green; varying between R.H.S. 146A and R.H.S. 146B.

Inflorescence:

*Number of flowers per inflorescence.*—Average 12.

*Blooming season.*—January through March in Northern Europe.

*Lastingness of blooms.*—Longer than two weeks.

*Blooms subiect to fading.*—Average 14 days.

*Stem.*—58 cm average length, 7 mm average diameter, brown in color, R.H.S. 200 A with tiny greyed-green spots, R.H.S. 191 B.

*Sepals.*—Shape: Broad elliptic. Description: 3 sepals smooth, top obtuse, base broad cuneate, margins entire. Upper Surface Color: Purple; R.H.S. N80C, lighter towards the margins; R.H.S. N80D. Markings (venation) darker: purple; varying between R.H.S. N78A and R.H.S. N78B. Lateral sepals have numerous dots at the base, average size 0.5 mm, purple in color, R.H.S. N79C. Lower Surface Color: Purple, varying between R.H.S. 76B and R.H.S. 76C, with green-white tints; varying between R.H.S. 157A and R.H.S. 157B. Lighter towards the margins. Markings (venation) only slightly darker: purple, R.H.S. 76A. Size: Average length 4.3 cm, average width 3 cm.

*Petals.*—Shape: 2 lateral petals reniform. Description: 2 lateral petals are smooth, top rounded, base broad acuminate. Upper Surface Color: Purple, R.H.S. N80C, lighter towards the margins, R.H.S. N80D; base darker; R.H.S. N80B. Markings (venation) darker, purple, varying between R.H.S. N78A and R.H.S. N78B.

*Lower surface color.*—Purple, varying between R.H.S. 76C and R.H.S. 76D. Size: (lateral petals) average length 4.1 cm, average width 4.8 cm.

*Labellum.*—Shape: Three-parted (lobed). Description: Lateral lobes rhomboidal/deltoid, top obtuse, dorsal lobe inverted deltoid, with two deltoid side-lobes; 7 mm long and 9 mm wide. Top cleft into two horn-like projections, which are twisted and curled. In between the two projections is a small deltoid lobe of 2 mm long and 3 mm wide. In the middle of the labellum (upper side), where the lobes meet, there is a small elevation, average height 5 mm, average width 5.5 mm, this elevation is cleft and almost two-parted. It is yellow in color, R.H.S. 9A with greyed-purple dots and stripes (R.H.S. 187B). Upper surface Color: Purple, from R.H.S. 71B to R.H.S. 72A, lateral lobes have a white base; R.H.S. 155A, striped greyed-purple; from R.H.S. 184A to R.H.S. 185A. Lower Surface Color: White, R.H.S. 155C, edged purple; R.H.S. 176A to red-purple; varying between R.H.S. 61A and R.H.S. 61B. Size: Lateral lobes: Average length 2.3 cm, average width 1.5 cm, dorsal lobe: average length 2.4 cm, average width 3.2 cm, the horn-like projections have an average length of 0.9 cm (bent upwards). Apex: Lateral lobes: obtuse, dorsal lobe cleft into two horn-like projections with a small deltoid lobe in between.

*Base.*—Lateral lobes cuneate, dorsal lobe acute.

*Raceme.*—Diameter: Average: 11 cm. Height: Average 25 cm (measured from lowest flower). Description (i.e. of branches with amount of flower buds): Flowering stem rounded, smooth and with a dull appearance. On the stems are several (on average 6) sheating leafy stipules, shaped broad deltoid, average length 6 mm, average width 16 mm, yellow-green in color, R.H.S. 148A. Average number of flowers and flower buds per stem: 10–15. Color: Blackish greyed-green, much darker than R.H.S. N189A, speckled greyed-green; R.H.S. 189A.

Reproductive organs: Column club-shaped, all reproductive organs are united in the column.

*Column.*—Length: Average 9 mm. Width: Average 6 mm. Color: Purple, R.H.S. N80B.

*Pollen.*—Pollen united in two stalked pollinia (pollen masses), pollinia shaped globular, average diameter 1 mm, orange; R.H.S. 24A.

*Stigma.*—Two stigmatic surfaces on top of the column, stigmas not stalked and unable to define as separate reproductive organs, but part of the column. Shape: The stigmatic surfaces are rounded, slightly convex. Dimension: Average diameter 2 mm, average height 0.5 mm. Color: White, R.H.S. 155A.

*Styles.*—No styles, the column holds both pollen and stigmas (stigmatic surfaces).

*Ovary.*—Dimension: Average length 4 mm, average width 2.5 mm. Color: White, R.H.S. 155A, flushed pink to greenish-white; R.H.S. 157B.

*Pedicel.*—Rounded, slightly glossy. Dimension: Average length 3 cm, average width 3 mm. Color: Yellow-green, varying between R.H.S. 144A and R.H.S. 144B.

Seed/fruit: No observations made.

Roots: Fleshy, rounded, slightly glossy, average diameter 5 mm, green; from R.H.S. 138A to R.H.S. 143A.

Pest disease resistance/susceptibility: No observation to date.

General observations: Broad elliptic leaves; brown stem; showy light purple flowers with dark purple stripes and white margins; dull, green leaves with silvery glance and purple spots; and freely flowering with 10–15 flowers and buds per raceme.

I claim:

1. A new and distinct cultivar of Phalaenopsis orchid plant named 'Osiris', as illustrated and described.

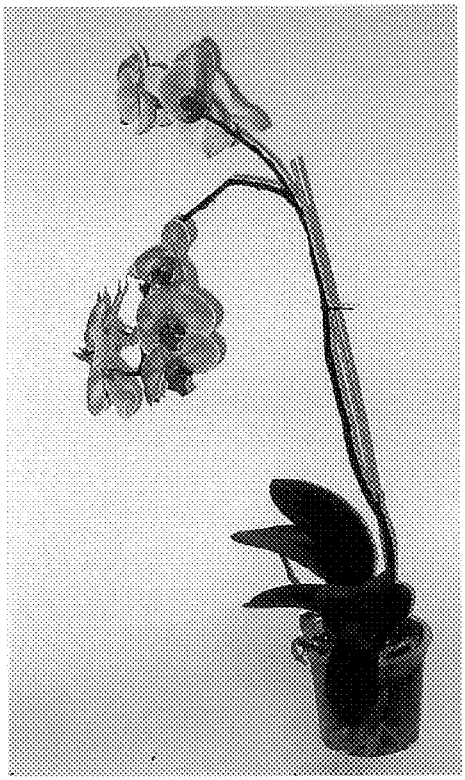
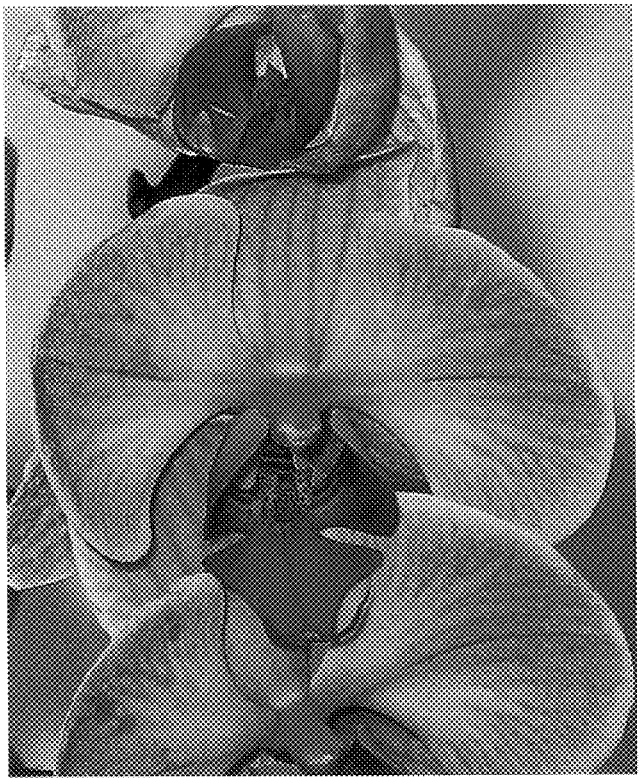

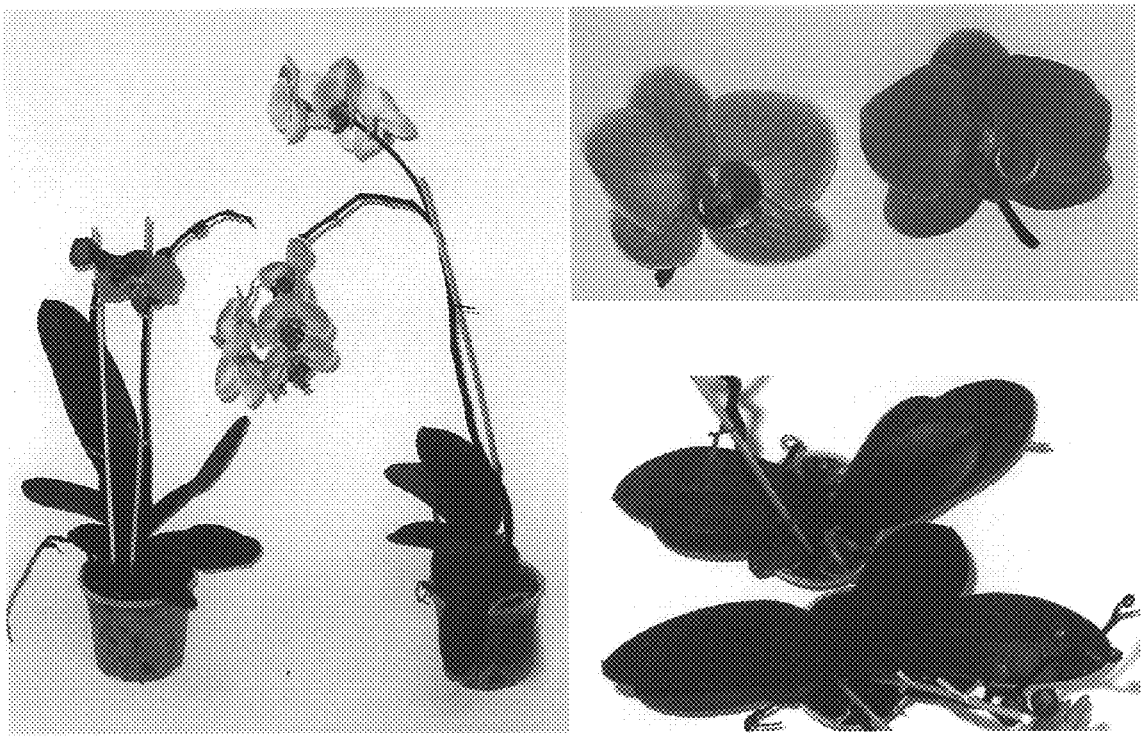

* * * * *